United States Patent [19]

Horodysky

[11] 4,440,656
[45] Apr. 3, 1984

[54] BORATED ALKOXYLATED ALCOHOLS AND LUBRICANTS AND LIQUID FUELS CONTAINING SAME

[75] Inventor: Andrew G. Horodysky, Cherry Hill, N.J.

[73] Assignee: Mobil Oil Corporation, New York, N.Y.

[21] Appl. No.: 323,519

[22] Filed: Nov. 23, 1981

[51] Int. Cl.$^3$ .......................... C10L 1/18; C10L 1/30; C10M 1/20; C10M 1/54
[52] U.S. Cl. ....................................... 252/49.6; 44/76; 252/389 R; 252/400 R; 568/1
[58] Field of Search ............. 252/49.6, 389 R, 400 R, 252/389.41, 400.41; 44/76; 568/1

[56] References Cited

U.S. PATENT DOCUMENTS 3,711,411  1/1973  Sawyer et al. ................. 252/49.6 X

FOREIGN PATENT DOCUMENTS 1474048  5/1977  United Kingdom ............... 252/49.6

*Primary Examiner*—W. J. Shine
*Attorney, Agent, or Firm*—Alexander J. McKillop; Michael G. Gilman; Claude E. Setliff

[57] ABSTRACT

Multifunctional additives are provided for fuel and lubricant compositions. The additives are borated alkoxylated alcohols, made by reacting the alkoxylated alcohol with a boron-containing compound such as boric acid or trialkyl borate. Lubricant and liquid fuel compositions containing such borated compounds are also provided.

18 Claims, No Drawings

BORATED ALKOXYLATED ALCOHOLS AND LUBRICANTS AND LIQUID FUELS CONTAINING SAME

BACKGROUND OF THE INVENTION

1. Field of the Invention

The invention relates to certain borated compounds and to lubricant and liquid fuel compositions containing them. In particular, it relates to borated derivatives of alkoxylated alcohols and to their use in liquid fuels and in lubricants to reduce friction and fuel consumption in internal combustion engines.

2. Discussion of the Prior Art

Alcohols, as are some carboxylates, are well known for their lubricity properties when formulated into lubricating oils and for their water-scavenging characteristics when blended into fuels. The use, for example, of vicinal hydroxyl-containing alkyl carboxylates such as glycerol monooleate have also found widespread use as lubricity additives. U.S. Pat. No. 2,788,326 discloses some of the esters suitable for the present invention, e.g. glycerol monooleate, as minor components of lubricating oil compositions. U.S. Pat. No. 3,235,498 discloses, among others, the same ester as just mentioned, as an additive to other oils. U.S. Pat. No. 2,443,578 teaches esters wherein the free hydroxyl is found in the acid portion, as for example in tartaric acid.

The above patents, as are numerous others, are directed to the use of such esters as additives. Other patents, such as U.S. Pat. Nos. 2,798,083; 2,820,014; 3,115,519; 3,282,971; and 3,309,318 as well as an article by R. R. Barnes et al. entitled "Synthetic Ester Lubricants" in Lubrication Engineering, August, 1975, pp. 454–457, teach lubricants prepared from polyhydric alcohols and acid containing no hydroxyl other than those associated with the acid function.

So far as is known, no effort has been made to employ borated alkoxylated alcohols as a fuel or lubricant additive. It is known that borated esters and related borates can be used in other areas. For example, U.S. Pat. No. 3,740,358 teaches a phenol-aldehyde foamable composition containing a boron compound, e.g. a material formed by reacting boric acid or boric oxide with such aliphatic hydroxyl-containing compound.

SUMMARY OF THE INVENTION

In accordance with the present invention there is provided a borated alkoxylated alcohol of the formula

wherein R is a hydrocarbyl group containing from 9 to 18 carbon atoms, R' is a hydrocarbylene group containing from 2 to 4 carbon atoms and x is 1–7. "Hydrocarbyl" can be cyclic or a straight or branched chain hydrocarbon group and can contain one or more unsaturated sites. The group is preferably alkyl and thus includes nonyl, decyl, dodecyl, tetradecyl and octadecyl. However, it is contemplated that the term also includes propylcyclohexyl, butylcyclohexyl, oleyl, stearyl, coco and mixtures thereof. It should be noted that it is often preferable to use alkoxylated alcohols that have been prepared using a mixture of alcohols. It can also be aryl, in which the aryl nucleus has 6 to 14 carbon atoms. "Hydrocarbylene" is preferably alkylene, including ethylene, propylene and butylene.

The invention also provides a lubricant or liquid fuel composition comprising a lubricant or fuel and a friction reducing or antiwear amount of the product. It is further contemplated that the product will aid in the reduction of fuel consumption in an internal combustion engine.

In the lubricant compositions, the product can be used in friction reducing amounts, which can range from about 0.01% by weight to about 5% by weight, preferably from 0.1 to 1%. The borated products also have significantly greater friction reducing properties, higher viscosity indices, good low temperature characteristics and solubility characteristics when used in low additive concentrations.

BACKGROUND OF THE INVENTION

It has now been found that boration of the disclosed alkoxylated alcohols significantly improves friction reducing properties and imparts an anti-oxidant component to these novel compositions. In addition to the friction reducing properties described, the alkoxylated alcohol borate esters possess much improved solubility characteristics, especially in synthetic fluids, over those of the non-borated derivatives. These borates are non-corrosive to copper, possess antioxidant and potential antifatigue characteristics.

While their preparation is not a part of this invention, it should nonetheless be noted that the alkoxylated alcohols are well known, as are methods for preparing them. In general, they can be made by reacting, in the presence of a catalyst, an alcohol with an epoxide such as ethylene or propylene oxide.

Boration of the above-described alkoxylated alcohols is accomplished with a boron compound, i.e., boron oxide ($B_2O_3$), or of the formula

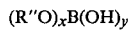

where
R" is a $C_1$ to $C_6$ alkyl, x is 0 to 3
and y is 0 to 3, the sum of x and y being 3.

The reaction can be performed in the presence of an alcoholic solvent, such as butanol or pentanol, or a hydrocarbon solvent such as benzene, toluene or xylene, or mixtures of such solvents. Reaction temperatures of 90° C. to 280° C. or more can be used. Reaction times can be 1 to 24 hours and more. Up to a stoichiometric amount of boric acid or alkyl borate is preferably used to produce a derivative containing from about 0.1% to about 10% of boron. At least 5 to 10% of the available hydroxyl groups on the alcohol can be borated to derive substantial beneficial effect. Conversely, a stoichiometric excess of boric acid (more than an equivalent amount of borating agent compared to alcohol hydroxyl groups) can also be charged to the reaction medium, resulting in a product containing the maximum amount of boron. The borated alcohol ethoxylates can also be borated with an alkyl borate such as tripropyl or tributyl borate, often in the presence of boric acid. Preferred reaction temperatures for boration with the acid is from about 110° C. to about 200° C. and with the borate from about 160° C. to about 240° C.

As disclosed hereinabove, the borated ester fluid is used with lubricating oils to the extent of from about 0.01% to about 5% by weight of the total composition. Furthermore, other additives, such as detergents, antioxidants, anti-wear agents and the like may be present. These can include phenates, sulfates, sulfonates, succinimides, amides, esters, zinc dithiophosphates, polymers, calcium and magnesium salts and the like.

The lubricants contemplated for use with the esters herein disclosed include mineral and synthetic hydrocarbon oils of lubricating viscosity, mixtures of mineral oils and synthetic oils, and greases from any of these. The synthetic hydrocarbon oils include long-chain alkanes such as cetanes and olefin polymers such as oligomers of hexane, octene, decene, and dodecene, etc. These products are especially effective in synthetic oils formulated using mixtures of synthetic hydrocarbon olefin oligomers and lesser amounts of ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of monocarboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic monocarboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyamines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long-chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention.

The liquid fuels contemplated include liquid hydrocarbon fuels such as fuel oils, diesel oils and gasolines and alcohol fuels such as methanol and ethanol or mixtures of these. These fuels contain 0.0001% to about 0.1% of the disclosed borate esters.

In the reaction described hereinabove, a solvent is preferred. Solvents that can be used include the hydrocarbon solvents, such as toluene, benzene, xylene, and the like, as well as the alcohol solvents such as propanol, butanol, pentanol and the like, and also mixtures of hydrocarbon solvents or alcohol solvents.

Having described the invention in general terms, the following are offered to specifically illustrate the development. It is to be understood they are illustrations only and that the invention shall not be limited except as limited by the appended claims.

EXAMPLE 1

Alcohol Ethoxylate $C_{12}$–$C_{15}$ alkanol triethoxylate was commercially obtained. It had an average molecular weight of 338 and contained approximately 3.0 ethylene oxide groups. The hydroxyl number was 166.

EXAMPLE 2

Borated Alcohol Ethoxylate

Approximately 175 g of $C_{12}$–$C_{15}$ alcohol triethoxylate described in Example 1 was charged to a 500 ml glass reactor equipped with agitator, Dean-Stark tube and slow nitrogen purge of vapor space. Approximately 13 g of boric acid and 50 g toluene was added and the reaction mixture was heated to 160° C. over a period of 6 hours until azeotropic distillation of water ceased. Approximately 12 g of water was collected. Solvent was removed by vacuum distillation and the product was filtered over diatomaceous earth to yield a clear, light-colored oil soluble fluid.

EXAMPLE 3

Borated Alcohol Ethoxylate

Approximately 1352 g of $C_{12}$–$C_{15}$ alcohol ethoxylate described in Example 1 was charged to a 3000 ml reactor equipped as described in Example 2. Approximately 85 g of boric acid and 150 g toluene was added. The reaction mixture was heated to 220° C. over a period of 7 hours until azeotropic distillation of water ceased. Approximately 73 g of water was collected. The toluene was removed by vacuum distillation and the product was filtered over diatomaceous earth to yield a clear, off-white, oil soluble fluid.

EXAMPLE 4

Alcohol Ethoxylate $C_9$–$C_{11}$ alkanol triethoxylate was commercially obtained. The alcohol ethoxylate contained approximately 2.6 moles of ethylene oxide per mole of $C_{9-11}$ alcohol, the molecular weight being approximately 274 and the hydroxyl number being 205.

EXAMPLE 5

Borated Alcohol Ethoxylate

Approximately 274 g of alcohol ethoxylate described in Example 4 was charged to a 1000 ml reactor equipped as described in Example 2. Approximately 22 g of boric acid and 50 g of toluene solvent were charged. The reactor mixture was heated to 195° C. over a period of 4 hours until azeotropic distillation of water ceased. The toluene was removed by vacuum distillation and the product was filtered over diatomaceous earth to yield a clear, light-colored oil soluble liquid.

It is believed that, depending upon the ratio of alkoxylated alcohol to boron compound, the temperature and other factors, the borated product included the following structure(s):

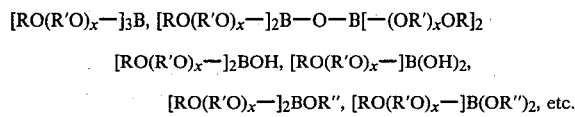

[RO(R'O)$_x$—]$_3$B, [RO(R'O)$_x$—]$_2$B—O—B[—(OR')$_x$OR]$_2$

[RO(R'O)$_x$—]$_2$BOH, [RO(R'O)$_x$—]B(OH)$_2$,

[RO(R'O)$_x$—]$_2$BOR'', [RO(R'O)$_x$—]B(OR'')$_2$, etc.

Since the exact composition of the product is unknown, the product claims themselves, as well as the composition claims, will be cast in terms of a reaction product.

The products were blended into a fully formulated 5W-20 synthetic automotive engine oil containing other additives, such as detergent, dispersant, anti-oxidant and the like additives and evaluated using the Low Velocity Friction Apparatus (LVFA) test.

EVALUATION OF PRODUCTS

The compound were evaluated as friction modifiers in accordance with the following test.

LOW VELOCITY FRICTION APPARATUS

Description

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction (U$_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed. Afterward, measurements of U$_k$ vs. speed are taken at 240, 300, 400, and 500 psi. Freshly polished steel specimens are used for each run. The surface of the steel is parallel ground to 4–8 microinches.

The data obtained are shown in Table 1. The data in Table 1 are reported as percent reduction in coefficient of friction at two speeds. The friction-reducing ester additives were evaluated in a fully formulated 5W-20 synthetic lubricating oil comprising an additive package including anti-oxidant, detergent and dispersant. The oil had the following general characteristics:

| | |
|---|---|
| Viscosity 100° C. | 6.8 cs |
| Viscosity 40° C. | 36.9 cs |
| Viscosity Index | 143 |

TABLE 1

| | | Frictional Properties | |
|---|---|---|---|
| | Additive Conc. in | % Change in Coefficient of Friction at | |
| Additive | Wt. % | 5 Ft./Min. | 30 Ft./Min. |
| Base Blend | — | 0 | 0 |
| Example 1 | 4 | 25 | 24 |
| Example 2 | 4 | 36 | 28 |
| Example 3 | 4 | 35 | 32 |
| | 2 | 35 | 32 |
| | 1 | 28 | 27 |
| | ½ | 12 | 11 |
| Example 5 | 4 | 37 | 32 |

The products of this invention were tested in a catalytic oxidation test for lubricants, using as the base oil a 200″ solvent paraffinic neutral mineral oil. The test lubricant composition is subjected to a stream of air bubbled through the composition at a rate of 5 liters per hour at 325° F. for 40 hours. Present in the composition are metals commonly used as materials of engine construction, namely:

a. 15.6 sq. in. of sand-blasted iron wire,
b. 0.78 sq. in. of polished copper wire;
c. 0.87 sq. in. of polished aluminum wire, and
d. 0.167 sq. in. of polished lead surface.

Inhibitors for oil are rated on the basis of prevention of oil deterioration as measured by the change in acid formation or neutralization number (%NN) and in kinematic viscosity (%KV) occasioned by the oxidation. The results of the tests are reported in Table 2.

TABLE 2

| | Catalytic Oxidation Test | | |
|---|---|---|---|
| Additive | Additive Conc. Wt. % | Lead Loss, mg | % Increase in Viscosity of Oxidized Oil (% KV) @ 210° F. | Neut. Number, NN |
| Base Oil | — | −1.2 | 67 | 3.62 |
| Example 2 | 1 | 0.0 | 21 | 2.98 |
| | 3 | — | 22 | 3.14 |
| Example 3 | 1 | 1.3 | 18 | 3.00 |
| | 3 | — | 20 | 3.26 |
| Example 4 | 1 | 0.3 | 18 | 3.40 |
| | 3 | — | 25 | 3.59 |

These borated compositions were non-corrosive to copper as measured in 200″ Solvent Paraffinic Neutral Lubricating Oil using the ASTM D130-80 Copper Strip Corrosivity Test.

TABLE 3

| | Copper Strip Corrosivity 3 Hours @ 250° F. | |
|---|---|---|
| Additive | Additive Conc. Wt. % | Test Rating |
| Example 2 | 1 | 1A |
| | 3 | 1A |

TABLE 3-continued

| | Copper Strip Corrosivity 3 Hours @ 250° F. | |
|---|---|---|
| Additive | Additive Conc. Wt. % | Test Rating |
| Example 5 | 1 | 1A |
| | 3 | 1A |

I claim:

1. A product of reaction obtained by reacting, at from about 90° C. to about 280° C., an alkoxylated alcohol of the formula $$RO(R'O)_xH$$

wherein R is a hydrocarbyl group containing 9 to 18 carbon atoms, R' is a hydrocarbylene group containing 2 to 4 carbon atoms and x is 1 to 7 with boron oxide or another boron compound of the formula $$(R''O)_xB(OH)_y$$

wherein R'' is an alkyl group containing 1 to 6 carbon atoms, x is 0 to 3 and y is 0 to 3, the sum of x and y being 3, the said product of reaction containing from about 0.1% to about 10% by weight of boron.

2. The product of claim 1 wherein the boron compound is boron oxide, boric acid or alkyl borate.

3. The product of claim 2 wherein the boron compound is boric acid.

4. The product of claim 1 wherein the alkoxylated alcohol is $C_{12}$ to $C_{15}$ alcohol triethoxylate and the boron compound is boric acid.

5. The product of claim 1 wherein the alkoxylated alcohol is $C_9$ to $C_{11}$ alcohol triethoxylate and the boron compound is boric acid.

6. A lubricant or liquid fuel composition comprising a major proportion of a lubricant or fuel and a friction reducing, antioxidant or anticorrosion amount of a product of reaction obtained by reacting, at from about 90° C. to about 280° C., an alkoxylated alcohol of the formula $$RO(R'O)_xH$$

wherein R is a hydrocarbyl group containing 9 to 18 carbon atoms, R' is a hydrocarbylene group containing 2 to 4 carbon atoms and x is 1 to 7 with boron oxide or another boron compound of the formula $$(R''O)_xB(OH)_y$$

wherein R'' is an alkyl group containing 1 to 6 carbon atoms, x is 0 to 3 and y is 0 to 3, the sum of x and y being 3, the said product of reaction containing from about 0.1% to about 10% by weight of boron.

7. The composition of claim 6, wherein the boron compound is boron oxide, boric acid or alkyl borate.

8. The composition of claim 7 wherein the boron compound is boric acid.

9. The composition of claim 6 wherein the alkoxylated alcohol is $C_{12}$ to $C_{15}$ alcohol triethoxylate and the boron compound is boric acid.

10. The composition of claim 6 wherein the alkoxylated alcohol is $C_9$ to $C_{11}$ alcohol triethoxylate and the boron compound is boric acid.

11. The composition of claims 6, 7, 8, 9 or 10 wherein the lubricant is (1) a mineral oil, (2) a synthetic oil, (3) mixtures of (1) and (2), or (4) a grease from (1), (2) or (3).

12. The composition of claim 11 wherein the lubricant is a mineral oil.

13. The composition of claim 11 wherein the lubricant is a synthetic oil.

14. The composition of claim 11 wherein the lubricant is a grease.

15. The composition of claim 6 wherein the liquid fuel is a liquid hydrocarbon fuel.

16. The composition of claim 6 wherein the liquid fuel is an alcohol fuel.

17. The composition of claim 6 wherein the liquid fuel is a mixture of liquid hydrocarbon fuel and alcohol fuel.

18. A method of reducing fuel consumption in an internal combustion engine which comprises the use therewith of a lubricant or fuel and a friction reducing amount of a product of reaction obtained by reacting, at from about 90° C. to about 280° C., an alkoxylated alcohol of the formula $$RO(R'O)_xH$$

wherein R is a hydrocarbyl group containing 9 to 18 carbon atoms, R' is a hydrocarbylene group containing 2 to 4 carbon atoms and x is 1 to 7 with boron oxide or another boron compound of the formula $$(R''O)_xB(OH)_y$$

wherein R'' is an alkyl group containing 1 to 6 carbon atoms, x is 0 to 3 and y is 0 to 3, the sum of x and y being 3, the said product of reaction containing from about 0.1% to about 10% by weight of boron.

* * * * *